US00PP25052P3

(12) United States Plant Patent
Suphachadiwong

(10) Patent No.: US PP25,052 P3
(45) Date of Patent: Nov. 11, 2014

(54) *PHALAENOPSIS* PLANT NAMED 'SUPHAL1310'

(50) Latin Name: ***Phalaenopsis* hybrid**
Varietal Denomination: SUPHAL1310

(71) Applicant: Thumrong Suphachadiwong, Chonburi (TH)

(72) Inventor: Thumrong Suphachadiwong, Chonburi (TH)

(73) Assignee: Suphachatawong Innovation (TH)

( * ) Notice: Subject to any disclaimer, the term of this patent is extended or adjusted under 35 U.S.C. 154(b) by 35 days.

(21) Appl. No.: 13/815,793

(22) Filed: Mar. 15, 2013

(65) Prior Publication Data

US 2014/0283257 P1 Sep. 18, 2014

(51) Int. Cl.
*A01H 5/00* (2006.01)

(52) U.S. Cl.
USPC ..... Plt./311

(58) Field of Classification Search
USPC ..... Plt./311
See application file for complete search history.

*Primary Examiner* — Kent L Bell
(74) *Attorney, Agent, or Firm* — Cassandra Bright

(57) ABSTRACT

A new and distinct *Phalaenopsis* cultivar named 'SUPHAL1310' is disclosed, characterized by small white flowers with a strong purple blush, long pointed downward lip of purple color with white apex and very open backward reflexed sepals, The new variety is a *Phalaenopsis*, typically produced as an indoor ornamental plant.

2 Drawing Sheets

Figure 1:
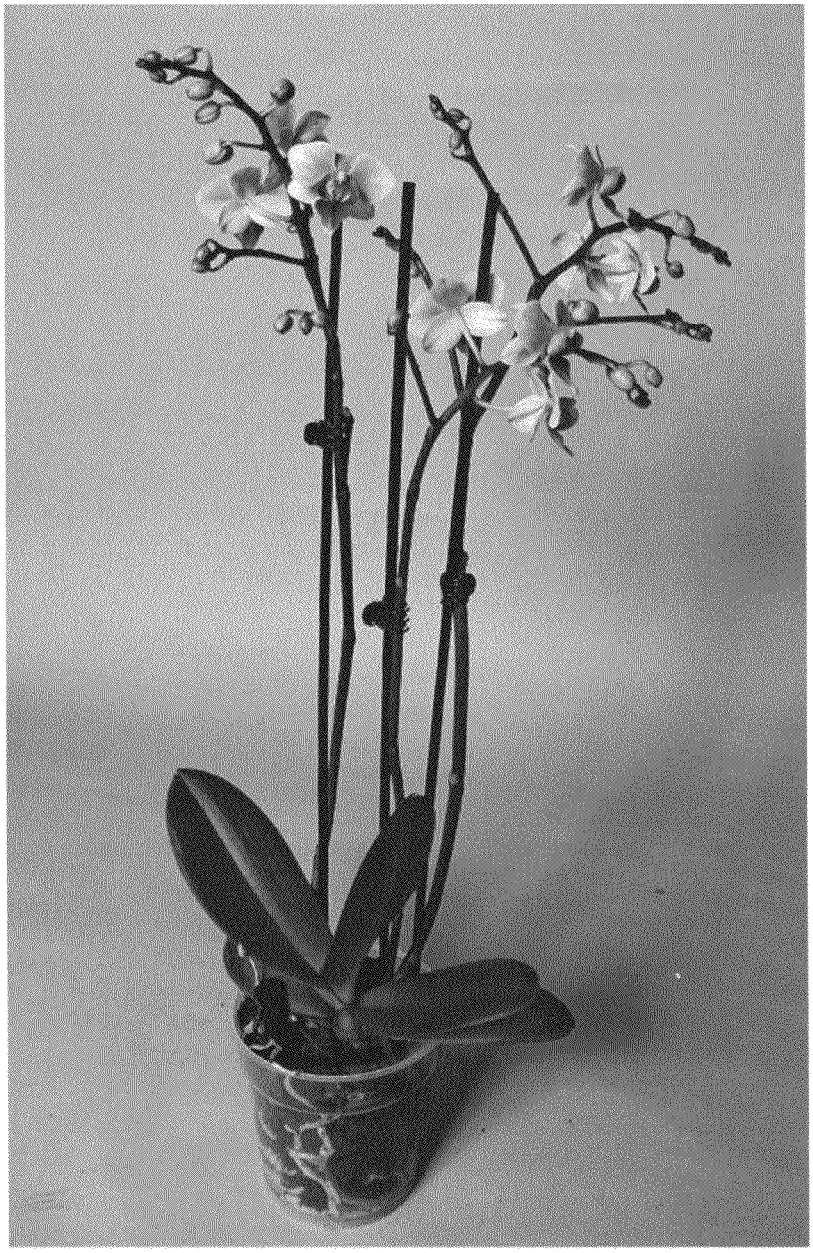

Latin name of the genus and species: *Phalaenopsis* hybrid. Variety denomination: 'SUPHAL1310'.

BACKGROUND OF THE INVENTION

This application relates to a new cultivar of *Phalaenopsis* hybrid. The new variety is the product of a planned breeding program. The new variety originated as a seedling from the crossing of the unpatented, proprietary seed parent *Phalaenopsis* 'PFMA2S7' with the unpatented, proprietary pollen parent referred to as *Phalaenopsis* 'SHH1S7'. The crossing was made by the inventor in his research greenhouse in Chonburi, Thailand in September of 2005.

The new variety was first selected by the inventor, Thumrong Suphachadiwong, a citizen of Thailand, in August of 2008 in a research greenhouse belonging to the inventor in Chonburi, Thailand. After identifying the new variety as a potentially interesting selection, the inventor continued confidential testing and propagation of 'SUPHAL1310', assessing stability of the unique characteristics of this variety.

Asexual reproduction of the new cultivar 'SUPHAL1310' was first performed at a commercial laboratory belonging to the inventor in Chonburi, Thailand by tissue culture in August of 2008. Access to all plants was restricted, as plants were kept in a greenhouse not open to the public, and tissue culture plantlets were in a laboratory belonging to the inventor, and not accessible to the public. Through subsequent propagation, multiple generations have been reproduced, which have shown that the unique features of this cultivar are stable and reproduced true to type.

SUMMARY OF THE INVENTION

The cultivar 'SUPHAL1310' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SUPHAL1310'. These characteristics in combination distinguish 'SUPHAL1310' as a new and distinct *Phalaenopsis* cultivar:

1. Small white flowers with a strong purple blush.
2. Lip color is purple with white apex.
3. Lip is long and pointed downward.
4. Sepals are very open and reflexed backwards away from the rest of the flower.

PARENT COMPARISON

Plants of the new cultivar 'SUPHAL1310' are similar to the seed parent, *Phalaenopsis* 'PFMA2S7' in most horticultural characteristics. The new variety, however, produces a bicolor flower compared to the single pink color flower of the seed parent. Additionally, the new variety produces much larger flowers than the seed parent.

Plants of the new cultivar 'SUPHAL1310' are similar to the pollen parent, *Phalaenopsis* 'SHH1S7' in most horticultural characteristics. Plants of the new variety however produce smaller flowers than the pollen parent. Additionally the new variety produces a more compact plant than the pollen parent.

COMMERCIAL COMPARISON

'SUPHAL1310' is similar to the unpatented commercial variety *Phalaenopsis* 'F1970' in most horticultural characteristics. However the new variety, 'SUPHAL1310' differs from 'F1970' in the following characteristics:

1. Different apical lobe shape.
2. Darker and narrower leaves.
3. Larger flowers.

4. More white parts on apical lobe.
5. Different petal and sepal shape.

'SUPHAL1310' is similar in most horticultural characteristics to the unpatented commercial variety *Phalaenopsis* 'F2616' in most horticultural characteristics. However the new variety, 'SUPHAL1310' differs from 'F2616' in the following characteristics:

1. Shorter narrower, darker green leaves.
2. Different petal and sepal shape.
3. More white areas on apical lobe.
4. Different lateral lobe shape.
5. Larger areas of purple coloration on petals and sepals.

BRIEF DESCRIPTION OF THE PHOTOGRAPH

The accompanying photographs in FIG. 1 illustrates in full color a typical plant of 'SUPHAL1310' grown in a commercial greenhouse in Zuidbroek, the Netherlands. This plant is approximately 18 months old after deflasking, shown planted in an 11 cm container.

Figure 2:
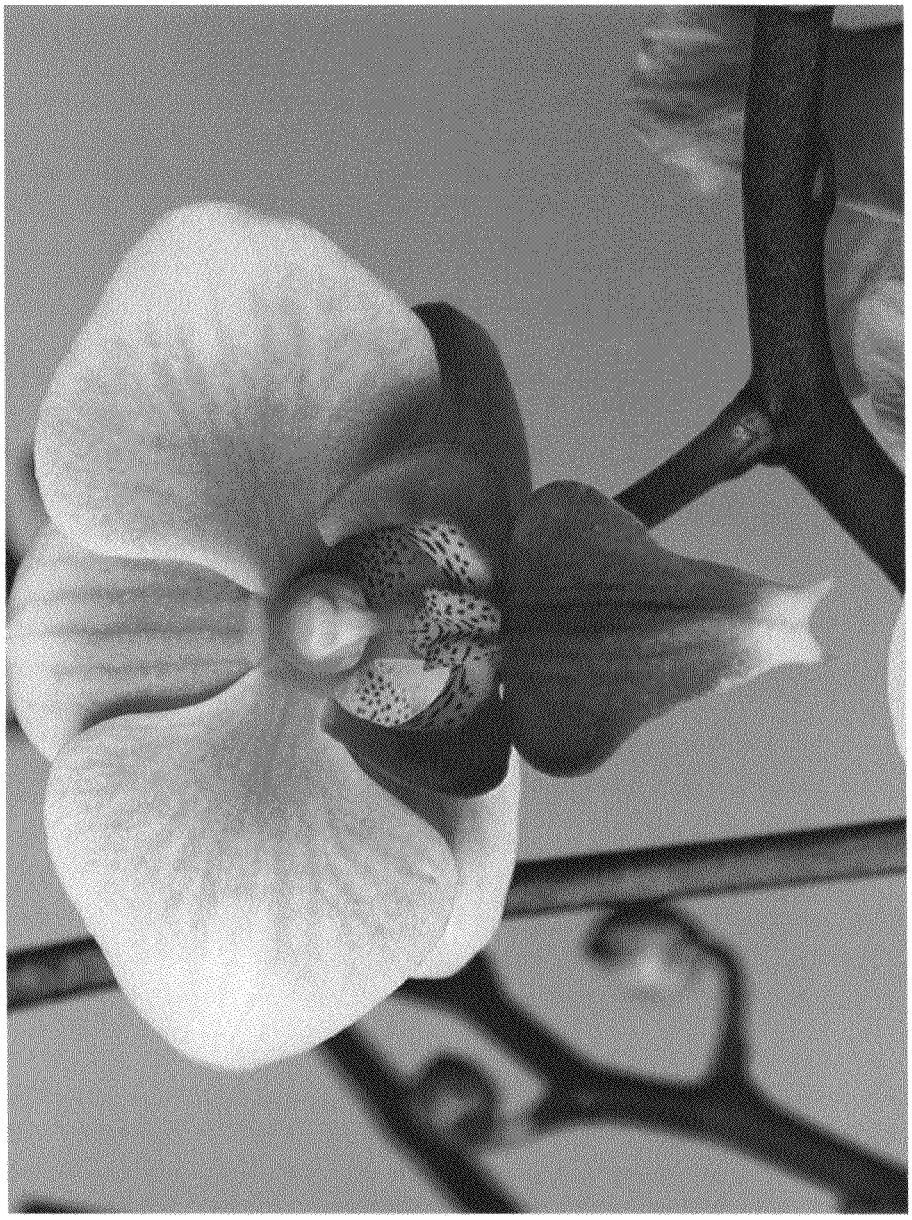

FIG. 2 illustrates a close up of the individual flower. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'SUPHAL1310' plants grown in a commercial greenhouse in Zuidbroek, the Netherlands. This plant is approximately 18 months old after deflasking, shown planted in an 11 cm container. Temperatures ranged between 18° C. and 28° C. day and night. No photoperiodic or chemical treatments were given to the plants. During bright Summer conditions, shade was given. During dark Winter months, supplemental light was given at unspecified amounts. Measurements and numerical values represent averages of typical plant types.

Botanical classification: *Phalaenopsis* hybrid 'SUPHAL1310'.

PROPAGATION

Type of propagation typically used: Tissue culture.

Time to initiate roots: About 21 days at approximately 28° C.

Time to produce a rooted cutting/liner: About 26 weeks at approximately 18° C. to 28° C.

Root description: Thick (typical for *Phalaenopsis*) and rounded, average diameter: 5 mm, colored greyed-green; near RHS 194A.

PLANT

Growth habit: Monopodial.

Height from top of soil line to top of foliage: Average 16.5 cm.

Height from top of soil line to top of flowers: Average 46.0 cm.

Plant spread: At widest, average: 25.8 cm; at narrowest: 24.6 cm.

Normal pot size: 11 cm.

Growth rate: Moderate.

Number of leaves per plant: Average 6.

FOLIAGE

Leaf:

*Arrangement*.—Distichous.

*Average length*.—Approximately 14.4 cm (including sheath).

*Average width*.—Approximately 5.7 cm.

*Shape of blade*.—Elliptic to narrow obovate.

*Aspect*.—Slightly to moderately upward.

*Apex*.—Unequal emarginated.

*Base*.—Cuneate. Sheath length: Average 1.4 cm. Sheath width: Average 1.1 cm. Sheath color: Green; near RHS 144B.

*Margin*.—Entire.

*Texture of top surface*.—Smooth, slightly furrowed.

*Texture of bottom surface*.—Smooth.

*Appearance of top surface*.—Slightly glossy.

*Appearance of bottom surface*.—Moderately glossy.

*Color*.—Young foliage upper side: Green; near RHS N137C. Young foliage under side: Yellow-green; near RHS 146C. Mature foliage upper side: Green; near RHS N137B. Mature foliage under side: Yellow-green; near RHS 146B.

*Venation*.—Type: Camptodromous. Venation coloration: Upper side green; slightly darker than near RHS N137C, main vein green; near RHS 147A, under side yellow-green; near RHS 146B main vein on under side green; near RHS 143A.

Petiole: No petioles present.

FLOWERING CHARACTERISTICS

Flower bud:

*Rate of opening*.—Approximately five days after stage described.

*Length*.—Approximately 1.5 cm.

*Diameter*.—Approximately 1.0 cm wide and 1.2 cm high.

*Shape*.—Broad ovate.

*Color*.—Yellow-green; near RHS 145C and 145D, upper side slightly tinged greyed-red; near RHS 182D.

Peduncle:

*Length*.—Approximately 47.1 cm.

*Width*.—Approximately 0.6 cm.

*Aspect*.—Approximately 60° angle to rosette.

*Strength*.—Strong.

*Texture*.—Smooth.

*Appearance*.—Very slightly glossy.

*Color*.—Yellow-green; near RHS 144A, darker towards the base; near RHS 147A, moderately to heavily dotted green; near RHS 143C.

Inflorescence:

*Flowers per stem*.—Average 21.

*Inflorescence arrangement*.—Compound panicle.

*Inflorescence height*.—Approximately 14.2 cm (measured from lowest branching of panicle to top of inflorescence).

*Inflorescence width*.—Approximately 16.8 cm.

Individual flowers:

*Flower type*.—Single zygomorphic flower.

*Shape*.—Rounded deltate.

*Length* (*height*).—Approximately 5.1 cm.

*Width*.—Approximately 4.8 cm.

*Depth*.—Approximately 2.9 cm.
*Fragrance*.—No fragrance.
*Persistent*.—Non-persistent.
*Quantity of petals*.—2 true petals.

Petals:
*Arrangement*.—One petal on each side of the column.
*Length*.—Approximately 2.3 cm.
*Width*.—Approximately 2.2 cm.
*Shape*.—Deltoid to short rhomboidal.
*Apex*.—Obtuse.
*Base*.—Cuneate.
*Margin*.—Entire.
*Texture*.—Upper (forward) surface: Smooth, velvety.
*Texture*.—Lower (back) surface: Smooth, velvety.
*Appearance*.—Matte on both surfaces.
*Color*.—When opening, forward surface: Purple-violet; near RHS N80C and N80D, top and margins white; near RHS NN155C. When opening, back surface: Purple; near RHS 76B, margins white; near RHSNN155D. Fully Opened, forward surface: Purple-violet; near RHS N80C and N80D, top and margins white; near RHS NN155C. Fully Opened, back surface: Purple; near RHS 76B, margins white; near RHS NN155C. Fading, forward surface: Not fading, only becoming non-velvety. Fading, back surface: Not fading, only becoming non-velvety.
*Color venation*.—Fully Opened, forward surface: Red-purple; near RHS 72B. Fully Opened, back surface.. Only main vein slightly visible, colored red-purple; near RHS 72B.

Labellum:
*Shape*.—Three-parted.
*Length*.—Approximately 2.4 cm.
*Width*.—Approximately 1.7 cm.
*Texture*.—Smooth, velvety.
*Appearance*.—Matte.
*Tip*.—Cleft, tips apiculate.
*Base*.—Cuneate.
*Color*.—When opening, forward surface: Central lobe red-purple; near RHS 72B, tinged more red towards the base; 71A, lateral lobes red-purple; near RHS 72A and 72B, base white; near RHS 155B, moderately dotted red-purple; near RHS 72A, callosities yellow; near RHS 9B, dotted red-purple; near RHS 71A. When opening, back surface: Central lobe purple; near RHS 76C and 76D, top white; near RHS NN155B, margins purple; near RHS 77B and 77C, tinged greyed-orange at the base; near RHS 165B, lateral lobes purple; near RHS 77B, lower margin darker; near RHS N77B, base white; near RHS 155C. Fully Opened, forward surface: Central lobe red-purple; near RHS 72B, tinged more red towards the base; 71A, lateral lobes red-purple; near RHS 72A and 72B, base white; near RHS 155B, moderately dotted red-purple; near RHS 72A, callosities yellow; near RHS 9B, dotted red-purple; near RHS 71A. Fully Opened, back surface: Central lobe purple; near RHS 76C to 76D, top white; near RHS NN155B, margins purple; near RHS 77B and 77C, tinged greyed-orange at the base; near RHS 165B, lateral lobes purple; near RHS 77B, lower margin darker; near RHS N77B, base white; near RHS 155C. Fading, forward surface: Not fading, only becoming non-velvety. Fading, back surface: Not fading, only becoming non-velvety.
*Color venation*.—Fully Opened, forward surface: No venation visible. Fully Opened, back surface: No venation visible. Margin: Entire.

Sepals:
*Quantity*.—3.
*Length*.—Dorsal sepal approximately 2.4 cm. Lateral sepals approximately 2.3 cm.
*Width*.—Dorsal sepal approximately 1.6 cm. Lateral sepals approximately 1.5 cm.
*Shape*.—Dorsal sepal elliptic. Lateral sepals ovate.
*Apex*.—Obtuse.
*Base*.—Broad cuneate.
*Margin*.—Entire.
*Texture*.—Smooth, velvety.
*Appearance*.—Matte.
*Color*.—Fully Opened, forward surface: Purple; near RHS N78D, veined darker; near RHS N78B, top and margins white; near RHS NN155D, lateral sepals with a conspicuous white spot at the base; near RHS NN155D, finely dotted purple; near RHS N78B. Fully Opened, back surface: Purple; near RHS 76C and 76D, veined slightly darker; near RHS 77C, with a darker spot near the top; near RHS 77B.

Pedicels:
*Length*.—Approximately 3.5 cm.
*Diameter*.—Approximately 0.25 cm.
*Angle*.—Approximately 85° to peduncle.
*Strength*.—Moderately strong.
*Texture*.—Smooth.
*Appearance*.—Moderately glossy.
*Color*.—Yellow-green; near RHS N144D, distal part lighter; near RHS 150D.

REPRODUCTIVE ORGANS

*Stamens, style and stigma fused into column?*.—Yes.
*Column length*.—Approximately 1.0 cm.
*Column diameter*.—Approximately 0.5 cm.
*Column color*.—Purple; near RHS N78B to N78C.
*Ovary*.—Position: Inferior. Diameter: Approximately 0.3 cm. Color: Purple; near RHS N78D.
*Pollen color*.—Yellow-orange; near RHS 23A.

OTHER CHARACTERISTICS

Disease resistance: Neither resistance nor susceptibility to the normal diseases found in *Phalaenopsis* has been observed.
Drought tolerance and cold tolerance: Normal for species.
Fruit/seed production: No fruits/seeds detected to date.

What is claimed is:

1. A new and distinct cultivar of *Phalaenopsis* plant named 'SUPHAL1310' as herein illustrated and described.

* * * * *